United States Patent [19]  
Batelaan

[11] 3,950,397  
[45] Apr. 13, 1976

[54] PROCESS FOR THE PREPARATION OF CITRIC ACID ESTERS, CITRIC ACID OR CITRIC ACID SALTS

[75] Inventor: Jan Gerardus Batelaan, Westervoort, Netherlands

[73] Assignee: Akzona Incorporated, Asheville, N.C.

[22] Filed: Dec. 6, 1974

[21] Appl. No.: 530,378

[30] Foreign Application Priority Data  
Dec. 7, 1973  Netherlands ..................... 7316762

[52] U.S. Cl. ...... 260/484 P; 260/482 P; 260/534 M; 260/535 P
[51] Int. Cl.² ......................................... C07C 59/16
[58] Field of Search .................... 260/535 P, 484 P

[56] References Cited  
UNITED STATES PATENTS  
3,798,266   3/1974   Bottaccio et al. ............... 250/535 P Primary Examiner—Lorraine A. Weinberger  
Assistant Examiner—P. J. Killos  
Attorney, Agent, or Firm—Stevens, Davis, Miller & Mosher

[57] ABSTRACT

A process is provided for making a triester of citric acid wherein the cyanohydrin of an acetone dicarboxylic acid diester is reacted with 1 to 3 molar equivalents of an aliphatic alcohol having 1 to 4 carbon atoms and at least two molar equivalents of anhydrous hydrogen chloride in an inert halogenated organic solvent for the cyanohydrin diester at not above 50°C. to form an imino ether, removing excess hydrogen chloride, adding water to form a two-phase system, separating the organic and water phases and recovering the resulting triester from the organic phase. The triester may be hydrolyzed into citric acid or a salt of citric acid in an acid or alkaline medium.

10 Claims, No Drawings

PROCESS FOR THE PREPARATION OF CITRIC ACID ESTERS, CITRIC ACID OR CITRIC ACID SALTS

The invention relates to an improved process for the preparation of citric acid esters, citric acid or the salts of citric acid.

A process for the preparation of citric acid or the salts of citric acid is known from Netherlands patent specification No. 7 302 863. In the process described in that specification, a dialkyl ester of acetone dicarboxylic acid is subjected to a cyanohydrin synthesis, followed by converting the resulting cyanohydrin, namely the 1,3-dicarbo-alkoxy-2-cyano-2 hydroxy propane, into citric acid under the influence of acid, and isolating the citric acid as such or as the salt of citric acid. In Example IV of the patent specification, the cyanohydrin obtained is converted into citric acid by direct hydrolysis with concentrated hydrochloric acid.

Such a method has the disadvantage that the hydrolysis proceeds extraordinarily slowly. It, moreover, results in the formation of $NH_4Cl$, which is difficult to isolate from citric acid. Citric acid is mainly used in the foodstuff industry, which makes very high demands on purity. It must therefore repeatedly be recrystallized for further purification.

A known and attractive method for the purification of carboxylic acids consists in that the acid is formed into an ester, which is purified by fractional distillation or re-crystallization and the pure ester is subsequently hydrolyzed with hydrochloric acid. The resulting acid, which is free from by-products, may then be made marketable for instance by crystallization. The preparation of the trialkyl ester of citric acid by direct esterification of the acid is unattractive. To obtain complete conversion, the water formed during the reaction must be removed continuously.

It is an object of the present invention to provide a process which no longer presents the above-mentioned drawbacks and is attractive for the preparation on an industrial scale of citric acid, salts of citric acid or the esters thereof.

The process provided by the invention is characterized in that the cyanohydrin of acetone dicarboxylic diester in the presence of an inert halogenated solvent is brought into reaction at a temperature not higher than 50° C. with 1 to 3 molar equivalents of an aliphatic alcohol having 1 to 4 carbon atoms and at least 2 molar equivalents of anhydrous HCl, followed successively by removing the excess HCl, addig water to obtain a two-layer system, heating, separating the organic layer and isolating the triester of citric acid from this layer, after which by hydrolysis in acid or an alkaline medium the triester may be converted into citric acid or a salt of citric acid and be isolated as such.

In the conversion of the cyanohydrin into the corresponding ester first of all an imino ether, also referred to as imidate, is formed in the presence of an alcohol and HCl. This reaction is known as the Pinner synthesis. It is described in *Chemical Reviews* 61 (1961), p. 181 ff. In this paper the decomposition of the imino ether as a result of the reaction with water is discussed on p. 191.

Just as the direct hydrolysis of a cyanohydrin by boiling in the presence of hydrochloric acid, the hydrolysis in accordance with the prior art by way of imino ether is very time consuming. Consequently, the reaction conditions commonly used in the preparation of imino ethers lead to very poor results in the preparation of the present imino ether both as far as the duration of the reaction and the yield are concerned. A number of steps which are generally presumed to lead to poor results in the preparation of imino ethers have surprisingly been found to give very good results when applied in the preparation of the present imino ether. For instance, the present process only leads to satisfactory results if use is made of halogenated solvent. On p. 181 of the above paper, however, it is stated that the use of a solvent is considered to be detrimental to the yield. Likewise, according to the present invention, it is considered of advantage to use at least two molar equivalents of HCl, whereas normally a slightly more than equivalent amount is recommended and on p. 188 of said paper it is, moreover, stated that an excess of chloride ions promotes the formation of acid amides.

The formation of acid amide being detrimental to the ester yield and the hydrolysis of the amide being attended with the formation of an equivalent amount of $NH_4Cl$, which is difficult to isolate from the citric acid, it might be concluded that a large excess of chloride ions should be avoided in any case.

It should be added that the use as such of a halogenated solvent in the presence of a aliphatic alcohol and a one to more than twofold excess of HCl for the conversion of a nitrile into an ester has been known from the British patent specification No. 1 260 954. In the British specification, the preparation of esters of thio- and oxydipropionic acid from the corresponding nitrile compounds is described. The long reaction times of 12 hours or longer, which are mentioned in the examples, will not induce a man skilled in the art to apply the steps proposed therein to a process which is directed to the industrial bulk production of citric acid and derivatives.

Moreover, in the British Patent Specification, halogenated solvents are mentioned in one breath with solvents such as benzene and toluene, which are not suitable for use in the present process. Also, the reactivity of the esters mentioned in the specification appears to be completely different from that of the citric triesters. Upon pouring the imino ether-containing reaction mixture into hot water, these triesters would immediately hydrolyze if the excess HCl were not first removed. The use of this process also results in the formation of large amounts of acid amides. Finally, mention should still be made of the German patent specification No. 562,290, which describes the preparation of α-hydroxycarboxylic esters from an aldehyde or ketone without isolation of the intermediately formed nitrile. The preparation is carried out in the presence of an inert solvent which may have been halogenated. As the water introduced in the preparation of nitrile remains in the reaction mixture, also the use of this process for the preparation of citric acid leads to the formation of large amounts of acid amide.

In the process provided by this invention, the starting materials is the cyanohydrin of acetone dicarboxylic diester. The nature of the alcohols of which the diesters are made up has substantially no predominant influence on the formation of the imino ether. The alcohols may be of an aliphatic, cyclic or aromatic character. They may contain 1 to 24 carbon atoms and may or may not carry substituents. Suitable substituents are for instance the halo groups such as fluoro, chloro, bromo and iodo; acyl groups, esterified or non-esterified carboxyl groups, and alkoxy groups, aryloxy groups, nitro groups, and the like.

Examples of suitable aliphatic or cyclic alcohols for making the diesters are: methanol, allyl alcohol, n-butanol, t-amylalcohol, cyclohexanol, stearylalcohol and the like. Examples of alcohols with an aromatic character are benzylalcohol, β-phenylethyl alcohol and cinnamic alcohol.

If the desired end product is citric acid or a salt derived therefrom, then the preferred starting material is a cyanohydrin of which the alcohols that make up the diester can be isolated from the reaction mixture in a simple manner. Suitable alcohols are, for instance, aliphatic alcohols with 1 to 4 carbon atoms, such as methanol, isopropanol, n-butanol, etc. After the alcohol has been isolated, it may be re-circulated. In that case, it may be of advantage if the alcohol used in the preparation of the imino ether is the same as the one of which the diester is made up.

If the desired end product is a citric triester made up of higher alcohols, then first an imino ether with a lower alcohol is prepared, which is ultimately converted into the triester. This triester is subsequently trans-esterified with the desired higher alcohol, the lower alcohol being removed by evaporation.

The formation of the imino ether takes place in the presence of an inert halogenated solvent. As solvents suitable for use in the process according to the invention may be mentioned, all halogenated aliphatic and cycloaliphatic hydrocarbons that display a good solubility for trialkyl esters of citric acid and from which the hydrogen chloride used can be readily removed after the formation of the imino ether.

As for practical reasons it is of advantage to carry out the process under atmospheric conditions, it is preferred to use solvents having a boiling point higher than 30° C. The same may be said for the upper limit of the boiling point. A solvent with a boiling point higher than about 200° C. can only be isolated from the triester under reduced pressure and is therefore not favorable for the economy of the process. As examples of solvents suitable for use in the process according to the invention may be mentioned: methylene chloride, methylene bromide, chloroform, bromoform, ethylene dibromide, ethylidene bromide, trichloroethylene, 1,1,1-trichloroethane, 1,1,2-trichloroethane, s-dichloroethylene, trimethylene bromide, pentamethylene bromide, fluor-containing compounds such as 1,2-difluortrichloroethane. It will be obvious that also mixtures of such solvents can be used.

For industrial application, it will be preferred to employ solvents having a favorable boiling point and a great difference in co-efficient of distribution for the triester on the one hand, and the diester amide on the other, in the two-phase system solvent/water, and a good resistance to hydrolysis. Moreover, the price of the solvent must not be unduly high. This is generally the case with halogenated hydrocarbons having from 1 up to 5 carbon atoms. It has been found that 1,2-dichloroethane is particularly suitable so it is preferred.

The amount of solvent to be used may vary between very wide limits and will generally differ from solvent to solvent. The amount must at least be such that after the hydrogen chloride has been removed by evaporation, and the organic layer has been poured into water, the extraction of the triester is optimal. For a man skilled in the art, it will not be difficult to determine for a given solvent the optimum ratio to the amount of cyanohydrin to be converted.

The amount of alcohol used in the preparation of the imino ether should, of course, be sufficient for the formation of the imino ether. In view of the reaction speed, it is preferred to use a more than equivalent amount. Because of the strong interaction between alcohol and hydrogen chloride not more than 3 molar equivalents of alcohol may be used. It is preferred to use it in an amount in the range of 1.1 to 1.5 molar equivalents. To prevent the reaction from taking too long, the preparation of the imino ether should be carried out in the presence of at least two molar equivalents of dry HCl. In this connection once again stress is laid on the importance of using a sufficient amount of solvent for the HCl, whose concentration in the liquid is also dependent on the pressure. The use of a slightly superatmospheric pressure may cause the HCl concentration to increase considerably. On the other hand, the chloride concentration must be prevented from reaching a level at which amide is formed. It has been found that very good results are obtained with an amount of 6 molar equivalents of HCl. The conversion was 90% of the theoretical yield and was reached in 20 minutes at a temperature 10° C. The fact that at a higher temperature the formation of amide increases should be taken into account in determining the optimum process conditions. The preparation of the triester according to the process of the invention is carried out by hydrolysis of the corresponding imino ether.

In order to prevent the formation of amide and further hydrolysis to citric acid or the mono or diesters thereof during the pouring out of the reaction mixture, which contains a large excess of HCl, the excess of HCl should first be removed as much as possible. This will generally be achieved by applying a slightly sub-atmospheric pressure.

In order to restrain the formation of amide the temperature at which the imino ether is formed must not be higher than 50° C. A temperature below 0° C., however, would favorably influence the reaction time. It has been found that an optimum reaction time may be obtained at a temperature in the range of 0° to 15° C.

Although the reaction of the cyanohydrin with an aliphatic alcohol and dry hydrogen chloride in the presence of a halogenated solvent such as 1,2-dichloroethane at 20° C. will be 90% after only 20 minutes, a 100% conversion will take considerably longer.

The invention therefore provides a process in which the reaction may be stopped before all the cyanohydrin has been converted, the reaction mixture, after the excess of HCl has been removed, is extracted with cold water and the nitrile-containing organic layer is recirculated, and the water layer in the presence of the same solvent as used in the conversion of the cyanohydrin is heated and extracted. The triester will then get into the solvent and the water layer will contain all the ammonium chloride the amide that may have formed and the half esters of citric acid. The ammonium chloride may be purified, if desired, by extraction with, for instance, acetone. The triester may be further treated in various ways.

For instance, the solvent may be removed by evaporation and the ester may be purified by distillation or recrystallization from water.

If pure acid is required, then the ester obtained after evaporation of the solvent and purified or not by recrystallization from water or distillation may while in a relatively concentrated state be boiled in the presence of, for instance, 6N HCl. After the volume of the solution has been reduced, if required, and after it has been cooled, citric acid free from organic byproducts will crystallize from the HCl solution. If the salt of citric acid is required, then the ester obtained after evaporation of the solvent and purified or not by recrystallization from water or distillation may while in a relatively concentrated state be boiled in the presence of a slight excess of an alkali, for instance, sodium hydroxide. The salt may also be prepared from the pure acid by neutralizing the latter with a stoechiometric amount up to a slight excess of alkali, after which the water may be evaporated.

In the above described way, it is possible to convert the cyanohydrin into citric acid in 97% yield in a period of about 70 minutes. The reaction time for obtaining the triester is, of course, even shorter.

The citric acid is of a purity suitable for use in foods.

The invention will be further described in the following examples which, of course, do not limit the scope of the invention.

EXAMPLE I (for comparison)

10 g of the cyanohydrin of the acetone dicarboxylic dimethyl ester were dissolved in 50 ml of methanol. Into this solution were passed 2 molar equivalents of dry hydrogen chloride. The reaction proceeded very slowly or not at all even after the reaction mixture had been heated to 65° C. After 7.3 molar equivalents of HCl had been added, it appeared that after 1 hour the cyanohydrin had entirely been converted at a temperature of 20° C. In an experiment carried out in the same way at 0° C. the reaction proceeded so slowly that after 17 hours still much nitrile was left.

After the excess of hydrogen chloride had been removed under reduced pressure, it was found after hydrolysis with water that the yield of trialkyl ester was relatively low and a considerable amount of amide had formed.

EXAMPLE II (for comparison)

9.6 g of the cyanohydrin of the acetone dicarboxylic dimethyl ester were dissolved in 50 ml of methanol. Into this solution were passed 8.2 g (= 4.7 molar equivalents) of dry hydrogen chloride in the presence of a small amount of water (0.94 g = 1.1 molar equivalents). The resulting mixture was kept for 24 hours at 20° C., after which practically all of the nitrile had been found to be converted. The reaction mixture was concentrated by evaporation and the residue was extracted with acetone. The extract contained 8.29 g of amide and 1.48 g of ester, which means that of the nitrile 80% had been converted into the amide and 13% into the ester. The residue (0.40 g) consisted of $NH_4Cl$. Consequently, in the preparation of the triester of citric acid via the imino ether route the presence of a small amount of water leads to the production of a large amount of acid amide, which is in contrast to the general results of the preparation of $\alpha$-hydroxy carboxylic esters according to the above-cited German patent specification No. 562,390.

EXAMPLE III (for comparison)

10 g of the cyanohydrin of the acetone dicarboxylic dimethyl ester were dissolved in 50 ml of methylacetate which still contained 3.5 ml of methanol. Adding 3.4 molar equivalents of HCl at 20° C. resulted in a too low reaction speed. But when the experiment was repeated with 5 molar equivalents of HCl at 20° C., the reaction was found to take 2 hours. After the excess of HCl had been removed, it turned out that only 38% had been converted into the triester and that the amide yield was 54%.

EXAMPLE IV (for comparison)

10 g of cyanohydrin of the acetone dicarboxylic dimethyl ester and 3 ml (1.3 molar equivalents) of methanol were dissolved in 50 ml of 1,2-dichloroethane. Into the resulting solution were passed 4 g (2.3 molar equivalents) of dry hydrogen chloride at 0° C. After 3 hours the conversion into imino ether was 96%. After 24 hours the conversion was found to be complete. In accordance with the process of the above-mentioned British patent specification No. 1 260 594 the reaction mixture was poured into 100 ml of water at 90° C. After evaporation of the dichloroethane (10 minutes) the reaction mixture was cooled and extracted with dichloroethane. The strongly acid water layer was extracted with n-butanol and the water removed by evaporation. The water layer contained 1.53 g of $NH_4Cl$. The organic layer was analyzed by liquid chromatography and was found to contain:

21.2% by weight of trimethyl citrate
21.8% by weight of dimethyl ester of citric amide
1.8% by weight of citric amide and the monomethyl ester thereof
38.6% by weight of mono and dimethyl citrate.

From the above it will be clear that the omission of the HCl removal prior to the addition of water leads to the formation of amide and that the acid medium moreover gives rise to considerable formation of half esters.

EXAMPLE V (Preparation of trimethyl citrate)

10 g of the cyanohydrin of the acetone dicarboxylic dimethyl ester and 3.0 ml (1.3 molar equivalents) of methanol were dissolved in 50 ml of dichloromethane. Into this solution was passed dry hydrogen chloride at 0° C. until saturation was reached. After the solution had been left overnight at this temperature, the excess HCl was sucked off at 0° C. and 10 ml of $H_2O$ were added. Next the reaction mixture was stirred for 5 hours at 20° C. The organic layer was isolated and concentrated by evaporation. The residue contained 10.67 g of trimethyl citrate, which corresponds to a yield of 91%. The water layer was found to contain 0.45 g of amide (4% of the theoretical yield) and 2.45 g of $NH_4Cl$.

EXAMPLE VI (Preparation of trimethyl citrate)

10 g of the cyanohydrin of the acetone dicarboxylic dimethyl ester and 3.5 ml (1.5 molar equivalents) of methanol were dissolved in 50 ml of 1,2-dichloroethane. Into this solution were passed 7 g (4 molar equivalents) of dry hydrogen chloride at 0° C. After 100 minutes the excess HCl was sucked off and the imino ether formed was extracted from the organic layer with cold water. The imino ether was obtained in 90% yield, based on the starting amount of nitrile. The water layer was mixed with an equal volume of fresh 1,2-dichloroethane, after which the mixture was heated to 50° C., with vigorous stirring. After 20 minutes the water layer containing the by-products was isolated and the organic layer concentrated by evaporation.

In this way pure trimethyl citrate was obtained in 95% yield, calculated on converted nitrile. The nonconverted nitrile (10% of the starting nitrile) was recovered from the organic layer of the first extraction.

EXAMPLE VII

The experiment of Example VI was repeated, but in such a way that 11 g of dry hydrogen chloride (6 molar equivalents) were passed into the solution. The reaction temperature was 10° C. After 20 minutes as much as 90% of the nitrile was found to have been converted. In the same way as described in Example VI the imino ether obtained was converted into the citric triester, which was isolated while in the pure state. The yield was 94%, calculated on converted nitrile. The trimethyl citrate was boiled for about 30 minutes in the presence of a solution of 6N HCl. After the solution had been concentrated, it was cooled and citric acid free from organic impurities crystallized from it.

EXAMPLE VIII 5 g of pure trimethyl citrate of example VI was boiled for about 15 minutes in a solution of 2N NaOH. After the evaporation of the methanol and non-converted ester, the solution was concentrated and sodium citrate free from organic impurities remained.

Although the invention has been described in detail for the purpose of illustration, it is to be understood that such detail is solely for that purpose and that those skilled in the art can make variations therein without departing from the spirit and scope of the invention except as it may be limited by the claims.

I claim:

1. A process for the preparation of a citric acid triester which comprises reacting the cyanohydrin of acetone dicarboxylic diester in the presence of an inert halogenated solvent at a temperature not higher than 50° C. with 1 to 3 molar equivalents of an aliphatic alcohol having 1 to 4 carbon atoms and at least 2 molar equivalents of anhydrous HCl, followed successively by removing the excess HCl, adding water to obtain a two-layer system, heating, separating the organic layer and isolating the triester of citric acid from this layer.

2. Process according to claim 1 wherein the inert halogenated solvent is 1,2-dichloroethane.

3. Process according to claim 1 wherien the conversion of the cyanohydrin takes place at a temperature in the range of about 0° to 15° C.

4. Process of claim 1 wherein the conversion of the cyanohydrin HCl is under a slight superatmospheric pressure.

5. Process of claim 1 wherein the reaction is stopped before all the cyanohydrin has been converted, the reaction mixture, after the excess of HCl has been removed, is extracted with cold water and the nitrile-containing organic layer is recirculated, and the water layer in the presence of the same solvent as used in the conversion of the cyanohydrin is heated and extracted.

6. Process of claim 1 wherein the citric triester is hydrolyzed with concentrated hydrochloric acid and after the alcohol has been evaporated and the solution been cooled the citric acid is crystallized from this same acid.

7. The process of claim 1 wherein the triester of citric acid is hydrolyzed in an acid medium to convert it into citric acid.

8. The process of claim 1 wherein the triester of citric acid is hydrolyzed in an alkaline medium to convert it into a salt of citric acid.

9. A process for preparing a triester of citric acid which comprises
reacting the cyanohydrin of an acetone dicarboxylic diester with from 1 to 3 molar equivalents of an aliphatic alcohol having 1 to 4 carbon atoms and at least two molar equivalents of anhydrous hydrogen chloride under substantially anhydrous conditions in an inert halogenated organic solvent for the said cyanohydrin of an acetone dicarboxylic acid diester at a temperature of not above 50° C. until an imino ether is formed,
separating excess hydrogen chloride from the reaction mixture,
mixing the reaction mixture with water to form a two-phase system of an organic layer and water layer,
separating the organic layer from the water layer, and recovering the resulting triester from the solvent.

10. The process of claim 9 wherein the alcohol is methanol and the solvent is 1,2-dichloroethane.

* * * * *